United States Patent
McCormack et al.

(10) Patent No.: US 6,589,638 B1
(45) Date of Patent: Jul. 8, 2003

(54) STRETCH-PILLOWED BULKED LAMINATE USEFUL AS AN IDEAL LOOP FASTENER COMPONENT

(75) Inventors: Ann Louise McCormack, Cumming, GA (US); William Bela Haffner, Kennesaw, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/929,561

(22) Filed: Sep. 15, 1997

(51) Int. Cl.[7] .................. B32B 3/06; B32B 27/12; B32B 31/04
(52) U.S. Cl. ............... 428/198; 442/394; 156/290; 428/99
(58) Field of Search ............. 428/198, 99; 442/394; 156/290

(56) References Cited

U.S. PATENT DOCUMENTS

| | | | |
|---|---|---|---|
| 3,692,618 A | | 9/1972 | Dorschner et al. ............. 161/72 |
| 3,765,974 A | * | 10/1973 | Petersik et al. .............. 428/198 |
| 3,802,817 A | | 4/1974 | Matsuki et al. ............... 425/66 |
| 3,855,046 A | | 12/1974 | Hansen et al. .............. 161/150 |
| D239,566 S | | 4/1976 | Vogt ........................... D59/2 R |
| 4,340,563 A | | 7/1982 | Appel et al. ................. 264/518 |
| 4,761,318 A | | 8/1988 | Ott et al. ....................... 428/85 |
| 5,032,122 A | | 7/1991 | Noel et al. .................. 604/391 |
| 5,223,329 A | * | 6/1993 | Amann ....................... 428/198 |
| 5,300,365 A | | 4/1994 | Ogale .......................... 428/461 |
| 5,326,612 A | | 7/1994 | Goulait ....................... 428/100 |
| 5,368,927 A | * | 11/1994 | Lesca et al. ................ 428/288 |
| D356,688 S | | 3/1995 | Uitenbroek et al. ........... D5/52 |
| 5,539,056 A | | 7/1996 | Yang et al. .................. 525/240 |
| 5,595,567 A | | 1/1997 | King et al. .................. 604/391 |
| 5,596,052 A | | 1/1997 | Resconi et al. ............. 526/127 |
| 5,614,281 A | | 3/1997 | Jackson et al. ............. 428/100 |
| 5,647,864 A | | 7/1997 | Allen et al. ................. 604/391 |

FOREIGN PATENT DOCUMENTS

| | | | |
|---|---|---|---|
| WO | 92/20251 | 11/1992 | ........... A44B/18/00 |
| WO | 97/24482 | 7/1997 | ............. D04H/1/54 |

OTHER PUBLICATIONS

Case No. 13257, patent application entitled "Breathable Filled Film Laminate" filed Sep. 15, 1997.
Case No. 13324, patent application entitled "Nonwoven Bonding Patterns Producing Fabrics with Improved Strength and Abrasion Resistance" filed Sep. 15, 1997.

* cited by examiner

Primary Examiner—Cheryl A. Juska
(74) Attorney, Agent, or Firm—William D. Herrick

(57) ABSTRACT

Disclosed is a composite material adapted for mechanical fastener use as the loop component complementary to a hook component. The composite material is made by laminating a film with an amorphous polymer layer to a prebonded nonwoven web, using a bond pattern different from the pattern on the nonwoven so as to provide loose filaments or fibers between the laminate bond points. Desirably, the composite also has a WVTR of at least about 100 g/m²/24 hours and a hydrohead of at least about 50 mbar. In use as a component of a disposable personal care product such as a disposable diaper, the loop fastener component may be substantially the entire backing to provide comfort, protection and highly variable fit.

22 Claims, 6 Drawing Sheets

STRETCH-PILLOWED BULKED LAMINATE USEFUL AS AN IDEAL LOOP FASTENER COMPONENT

BACKGROUND OF THE INVENTION

1. Field of the Invention

The present invention relates to composite materials which can be designed to have breathable barrier applications and which may be particularly useful as a component of fasteners of the hook and loop type typified by those extensively marketed by VELCRO INTERNATIONAL and now available from numerous sources for applications from shoe ties to golf gloves and many others where nonpermanent attachment is desired. These fasteners fundamentally include a hook member and a loop member that, when pressed together, entangle in a manner that resists shear forces but can be separated when subjected to a desired level of peel force. The design of these members has become quite sophisticated and provides a wide range of properties obtainable by varying factors such as hook shape, size and flexibility as well as similar loop features. For many low cost applications such as fasteners for disposable garment applications like diapers and adult incontinent wear, it has been necessary to develop inexpensive manufacturing techniques and materials for such fasteners that, nevertheless, meet the performance requirements. Particularly for such applications where the loop component also serves as the backing material, it is highly desirable that it can be breathable for comfort and also that it serve as a barrier to prevent leakage. The present invention provides a composite of film and nonwoven fabric for use as an ideal loop fastener component particularly suited to such disposable product applications.

2. Background

The art is replete with references to hook and loop type fasteners and components for such fasteners intended for use in disposable product applications such as disposable diapers and the like. Just by way of example, reference may be had to coassigned U.S. Pat. No. 5,614,281 to Jackson et al. which, itself, provides much background information and for that purpose is incorporated herein by reference in its entirety. Other loop fastener materials are described in, for example, U.S. Pat. No. 4,761,318 to Ott et al., U.S. Pat. No. 5,032,122 to Noel et al., U.S. Pat. No. 5,326,612 to Goulait, U.S. Pat. No. 5,595,567 to King et al, and U.S. Pat. No. 5,647,864 to Allen et al. Briefly, a particularly economical loop component may be formed using nonwoven manufacturing techniques such as spunbonded processes that result in significant areas of the web between bond points where the filaments are unbonded to each other and available to engage hooks of a complementary hook member. Factors, such as configuration, number and area coverage of the bonds in the nonwoven as well as the selection of a particular hook member, may be varied to achieve a desired level of peel strength and other properties within a designated cost range. In addition, the selection of a polymer or other compositional ingredient for the nonwoven and/or the hook component can affect the performance and/or cost of the fastener in a given application. There remains a need for a loop fastener component that can have tailored properties such as peel strength, shear strength and refastenability as well as barrier and, if desired, breathability functions at a cost consistent with use as a backing component of disposable products. Other uses for breathable barrier materials having clothlike attributes such as surgical gowns and drapes, for example, will be apparent to those skilled in the art.

SUMMARY OF THE INVENTION

The present invention is directed to a nonwoven and film composite material that can include properties making it particularly adapted for use as a loop fastener component that includes a laminate of a film layer and a prebonded nonwoven layer wherein the laminate bonds are separate and independent of the bond sites of the prebonded nonwoven while leaving filaments or fibers between such laminate bond sites both bonded and unbonded. For improved comfort and utility as a backing component of a personal care product such as a disposable diaper, for example, the laminate can be breathable with a moisture vapor transmission rate above about 100 $g/m^2/24$ hours and can have a hydrohead value of at least 50 mbar. In use with a complementary hook component, a loop fastener formed from this composite provides capability for fastening anywhere on the backing of the product and consistent refastenability over a period of time and for the number of cycles of opening and closing that is suitable for many disposable and limited use applications. The nonwoven layer contains a bond pattern of either uniform or nonuniform bond impressions that result in an unbonded area of at least 70%, taken over any 100 cm square of nonwoven surface. In addition the bond frequency provides a pattern density in the range of from about 50 to about 200 bonds/$in.^2$ with an area coverage of from about 5% to about 30%, advantageously from about 10% to about 25%. The film layer is either a multilayer or coextruded structure with an exposed layer of a soft, amorphous polymer, or a monolayer and, in either case, is a predominantly microporous barrier to liquid that is conformable and compatible with the nonwoven. Lamination may be achieved by an application of heat and pressure taking advantage of the amorphous polymer properties either in the multilayer film, or as the separately applied bonding layer in the monolayer film embodiment, for example. The independent laminate bond pattern is selected so that areas between the laminate bonds contain separate nonwoven bonds that further integrate the fibers or filaments of the nonwoven surface. For example, laminate bond patterns may have less than 50% coverage of the laminate surface area, advantageously less than about 30% and may be uniform or nonuniformly shaped and/or configured and will generally be significantly fewer in number than the nonwoven prebonds. To enhance clothlike aesthetics and engagement of hook elements for the loop component applications, a retracted laminate may be formed by stretching the film prior to lamination to the nonwoven and subsequently allowing the laminate to relax or retract, producing a pillowed/highly bulked nonwoven film laminate between bond areas where the film and nonwoven remain securely attached. The invention also includes the method for making the composite.

DETAILED DESCRIPTION

Definitions

As used herein the following terms have the specified meanings, unless the context demands a different meaning, or a different meaning is expressed; also, the singular generally includes the plural, and the plural generally includes the singular unless otherwise indicated.

"Nonwoven" means a web of fibers or filaments that is formed by means other than knitting or weaving and that contains bonds between some or all of the fibers or filaments; such bonds may be formed, for example, by thermal, adhesive or mechanical means such as entanglement.

"Fiber" means an elongated strand of defined length, such as staple fibers formed by cutting a continuous strand into lengths of, for example, 2 to 5 cm. Collections of fibers may have the same or different lengths.

"Filament" means a generally continuous strand that has a very large ratio of length to diameter, for example, 1000 or more.

"Spunbond" means a nonwoven of filaments formed by melt extrusion of a polymer into strands that are quenched and drawn, usually by high velocity air, to strengthen the filaments which are collected on a forming surface and bonded, often by the patterned application of heat and pressure. Spunbonded processes are described, for example, in the following patents to which reference may be made for additional details: U.S. Pat. No. 4,340,563 to Appel et al., U.S. Pat. No. 3,802,817 to Matsuki et al., and U.S. Pat. No. 3,692,618 to Dorschner et al.

"Loop" means an area of separation of at least one fiber or filament from others in a nonwoven and includes but is not limited to configurations where the same fiber or filament intersects itself; i.e. a complete circle or oval, for example, need not be formed.

"Complementary hook" means a structure adapted for use as a mechanical fastener component and having projections of a profile, height, density, geometry and orientation so as to releasably attach to a loop fastener material of the invention and provide the intended level of hook peel and shear strength properties. The projections need not form a "hook" but may have other configurations such as a mushroom shape, for example. Suitable hook materials may be unidirectional or bidirectional, for example, and often comprise from about 16 to about 620 hooks per square centimeter and hook heights of from about 0.00254 cm to about 0.19 cm. They are available, for example, from Velcro International of Manchester, N.H. and 3M of St. Paul, Minn.

"Amorphous Polymer" when used herein to describe a bonding layer either as a multilayer film component or separately applied layer means a thermoplastic polymer such as certain polyolefins with a density in the range of from about 0.85 to about 0.89 and low crystallinity, for example, less than about 30% such as those frequently used as components of adhesives and having limited hot melt properties.

"Thermal point bonding" involves passing a fabric or web of fibers to be bonded between a heated calender roll and an anvil roll. The calender roll is patterned in some way so that the entire fabric is not bonded across its entire surface. As a result, many patterns for calender rolls have been developed for functional as well as aesthetic reasons. As will be understood by those skilled in the art, bond area percentages are, of necessity, described in approximations or ranges since bond pins are normally tapered and wear down over time. As those skilled in the art will also recognize, references to "pins/in.$^2$" and "bonds/in.$^2$" are somewhat interchangeable since the anvil pins will create bonds in the substrate in essentially the same sizes and surface relationship as the pins on the anvil. For the nonwoven, one example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin may have a side dimension of 0.038 inches (0.965 mm), for example, resulting in a pattern having a bonded area of about 30%. Another typical point bonding pattern is the expanded Hansen and Pennings or "EHP" bond pattern which produces a bond area of about 15% to 18% which may have a square pin having a side dimension of 0.037 inches (0.94 mm), for example, and a pin density of about 100 pins/in$^2$. Another typical point bonding pattern designated "714" has square pin bonding areas wherein each pin may have a side dimension of 0.023 inches, for example, for a bond area of 15% to 20% and about 270 pins/in$^2$. Other common patterns include a "Ramisch" diamond pattern with repeating diamonds having a bond area of 8% to 14% and 52 pins/in.$^2$ as well as a wire weave pattern looking as the name suggests, e.g. like a window screen and having a bond area of 15% to 20% and 302 pins/in.$^2$. Typically, the percent bonding area varies widely from around 10% to around 30% of the area of the fabric laminate web and the number of pins/in$^2$ also may vary over a wide range. Of the practically limitless combinations of bond configurations, however, only selected bond patterns are useful in accordance with the invention. These will have a bond area in the range of from about 5% to about 30%, desirably in the range of from about 10% to about 25% and a pin density in the range of from about 50 to about 200 per square inch, desirably in the range of from about 75 to about 125 per square inch. When used herein, the term "prebonded" nonwoven means those nonwovens having been bonded with a pattern defined as useful in accordance with these parameters. As is well known in the art, the spot bonding holds the laminate layers together as well as imparts integrity to each individual layer by bonding filaments and/or fibers within each layer.

Examples of laminate bond decorative patterns used to overbond or laminate the prebonded nonwoven to the film are C-Stars and Baby Objects as shown in FIGS. 5 and 6. The C-Star pattern has a cross-directional bar or "corduroy" design interrupted by shooting stars and generally has a percent bond area of about 17% and the Baby Objects pattern (also illustrated in coassigned U.S. Design Pat. No. 356,688 to Uitenbroek et al. dated Mar. 28, 1995) has a percent bond area in the range of from about 12% to about 20%.

Test Procedures

Hydrohead: A measure of the liquid barrier properties of a fabric is the hydrohead test. The hydrohead test determines the height of water (in mbars) which the fabric will support before a predetermined amount of liquid passes through. A higher hydrohead reading indicates that a fabric is a better barrier to liquid penetration than a fabric with a lower hydrohead. The hydrohead test is performed according to Federal Test Standard 191A, Method 5514.

Grab Tensile test: The grab tensile test is a measure of breaking strength and elongation or strain of a fabric when subjected to unidirectional stress. This test is known in the art and conforms to the specifications of Method 5100 of the Federal Test Methods Standard 191A. The results are expressed in pounds or grams to break and percent stretch before breakage. Higher numbers indicate a stronger, more stretchable fabric. The term "load" means the maximum load or force, expressed in units of weight, required to break or rupture the specimen in a tensile test. The term "total energy" means the total energy under a load versus elongation curve as expressed in weight-length units. The term "elongation" means the increase in length of a specimen during a tensile test. The grab tensile test uses two clamps, each having two jaws with each jaw having a facing in contact with the sample. The clamps hold the material in the same plane, usually vertically, separated by 3 inches (76 mm) and move apart at a specified rate of extension. Values for grab tensile strength and grab elongation are obtained using a sample size of 4 inches (102 mm) by 6 inches (152 mm), with a jaw facing size of 1 inch (25 mm) by 1 inch, and a constant rate of extension of 300 mm/min. The sample is wider than the clamp jaws to give results representative of effective strength of fibers in the clamped width combined with additional strength contributed by adjacent fibers in the fabric. The specimen is clamped in, for example, a Sintech 2 tester, available from the Sintech Corporation, 1001 Sheldon Dr., Cary, N.C. 27513, an Instron Model ™, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154. This closely simulates fabric stress conditions in actual use. Reported results are the average of three specimens tested and the test may be performed with the specimens in the cross direction (CD) or in the machine direction (MD).

Strip Tensile: The strip tensile test is similar to the grab tensile and measures the peak and breaking loads and peak and break percent elongations of a fabric. This test measures the load (strength) in grams and elongation in percent. In the strip tensile test, two damps, each having two jaws with each jaw having a facing in contact with the sample, hold the material in the same plane, usually vertically, separated by 3 inches and move apart at a specified rate of extension. Values for strip tensile strength and strip elongation are obtained using a sample size of 3 inches by 6 inches, with a jaw facing size of 1 inch high by 3 inches wide, and a constant rate of extension of 300 mm/min. The Sintech 2 tester, available from the Sintech Corporation, 1001 Sheldon Dr., Cary, N.C. 27513, the Instron Model ™, available from the Instron Corporation, 2500 Washington St., Canton, Mass. 02021, or a Thwing-Albert Model INTELLECT II available from the Thwing-Albert Instrument Co., 10960 Dutton Rd., Phila., Pa. 19154 may be used for this test. Reported results are the average of three specimens tested and the test may be performed with the specimen in the cross direction (CD) or in the machine direction (MD).

Peel test: In peel or delamination testing a laminate is tested for the amount of tensile force which will pull the layers of the laminate apart. Values for peel strength are obtained using a specified width of fabric, clamp jaw width and a constant rate of extension. For samples having a film side, the film side of the specimen is covered with masking tape, or some other suitable material, in order to prevent the film from ripping apart during the test. The masking tape is on only one side of the laminate and so does not contribute to the peel strength of the sample. This test uses two clamps, each having two jaws with each jaw having a facing in contact with the sample, to hold the material in the same plane, usually vertically, separated by 2 inches to start. The sample size is 4 inches wide by as much length as necessary to delaminate enough sample length. The jaw facing size is 1 inch high by at least 4 inches wide, and the constant rate of extension is 300 mm/min. The sample is delaminated by hand a sufficient amount to allow it to be clamped into position, and the clamps move apart at the specified rate of extension to pull the laminate apart. The sample specimen is pulled apart at 180° of separation between the two layers, and the peel strength reported is an average of three tests, peak load in grams. Measurement of the force begins when 16 mm of the laminate has been pulled apart, and it continues until a total of 170 mm has been delaminated. The Sintech 2 tester, available from the Sintech Corporation, 1001 Sheldon Dr., Cary, N.C. 27513, the Instron Model ™, available from the Instron Corporation, 2500 Washington St., Canton, Mass. 02021, or the Thwing-Albert Model INTELLECT II available from the Thwing-Albert Instrument Co., 10960 Dutton Rd., Phila., Pa. 19154, may be used for this test. The test may be performed with the specimen in the cross direction (CD) or in the machine direction (MD).

Martindale Abrasion test: This test measures the relative resistance to abrasion of a fabric. The test results are reported on a scale of 1 to 5, with 5 being the least wear and 1 the most, after 120 cycles with a weight of 1.3 pounds per square inch. The test is carried out with a Martindale Wear and Abrasion Tester such as model no. 103 or model no. 403 available from James H. Heal & Company, Ltd. of West Yorkshire, England. The abradant used is a 36 inch by 4 inch by 0.05 inch thick silicone rubber wheel reinforced with fiber glass having a rubber surface hardness 81A Durometer, Shore A of 81 plus or minus 9. The abradant is available from Flight Insulation Inc., a distributor for Connecticut Hard Rubber, 925 Industrial Park, NE, Marietta, Ga. 30065.

Basis Weight: the basis weights of various materials described herein were determined in accordance with Federal Test Method No. 191A/5041. Sample size for the sample materials was 15.24×15.24 centimeters, and three values were obtained for each material and then averaged. The values reported below are the averages.

Hook Peel: the 180° peel strength test is intended to measure how well hook and loop components engage and it involves attaching a hook material to a loop material of a hook and loop fastening system and then peeling the hook material from the loop material at a 180° angle. The maximum load is recorded in grams as an average of the three highest peak load values needed to disengage or peel the two materials. To perform the test, a continuous rate of extension tensile tester with a 5000 gram full scale load is required, such as a Sintech System 2 Computer Integrated Testing System available from Sintech, Inc., having offices in Research Triangle Park, N.C. A 3 inch (7.6 cm) by 6 inch (15.2 cm) sample of the loop material is used. A 2.5 inch (6.3 cm) wide sample of hook material, which is adhesively and ultrasonically secured to a substantially inelastic, nonwoven material, is positioned hook side down over and applied to the upper surface to cover the loop material sample with about a one inch overlap. To ensure adequate and uniform engagement of the hook material to the loop material, a wringer, Model LW 1, part number 14-9969 from Atlas Electric Devices Co., Chicago, Ill. is used to squeeze the combined hook and loop materials for one cycle, with one cycle equaling a pass through the wringer using a total of 40 pounds weight. One end of the fingertab material supporting the hook material is secured within the upper jaw of the tensile tester, while the end of the loop material directed toward the upper jaw is folded downward and secured within the lower jaw of the tensile tester. The placement of the respective materials within the jaws of the tensile tester should be adjusted such that minimal slack exists in the respective materials and the gage length is 3 inches (7.6 cm) prior to activation of the tensile tester. The hook elements of the hook material are oriented in a direction generally perpendicular to the intended directions of movement of the tensile tester jaws. The tensile tester is activated at a constant rate of separation of 500 mm per minute and the peak load in grams to disengage or peel the hook material from the loop material at a 180° angle is then recorded, based on the average of the three highest peaks.

Hook Shear the dynamic shear strength test involves engaging a hook material to a loop material of a hook and loop fastening system and then pulling the hook material across the loop material's surface. The maximum load required to disengage the hook from the loop is measured in grams. To conduct this test, a constant rate of extension tensile tester with a 5000 gram full scale load is required, such as Sintech System 2 Computer Integrated Testing System. A 3 inch by 6 inch sample of the loop material is attached with masking tape to a flat support surface. A sample of hook material 2.5 in.×0.76 in., which is adhesively and ultrasonically secured to a substantially inelastic, nonwoven material, is positioned over and applied to the upper surface of the loop material sample centered in the shorter direction and 2 inches in from the cut edge. To ensure adequate and uniform engagement of the hook material to the loop material, a wringer, Model LW 1, part number 14-9969 from Atlas Electric Devices Co., Chicago, Ill. is used to squeeze the combined hook and loop materials for one cycle, with one cycle equaling a MD (longer dimension) pass, through the wringer using a total of 40 pounds weight. One end of the nonwoven material supporting the hook material is secured within the upper jaw of the tensile tester, and the end of the loop material directed toward the lower jaw is secured within the lower jaw of the tensile tester. The placement of the respective materials within the jaws of the tensile tester should be adjusted such that minimal slack exists in the respective materials prior to activation of the tensile tester. The hook elements of the hook material are oriented in a direction generally perpendicular to the intended directions of movement of the tensile tester jaws. The tensile tester is activated at a gage length of 3 inches and crosshead speed of 250 mm per minute and the peak load in grams to disengage the hook material from the loop material is then recorded in grams as the average of the highest peaks for three specimens.

DETAILED EMBODIMENTS

The invention will be described with reference to the drawings and examples which illustrate certain embodiments. It will be apparent to those skilled in the art that these embodiments do not represent the full scope of the invention which is broadly applicable in the form of variations and equivalents as may be embraced by the claims appended hereto. It is intended that the scope of the claims extend to all such variations and equivalents.

Figure 1:
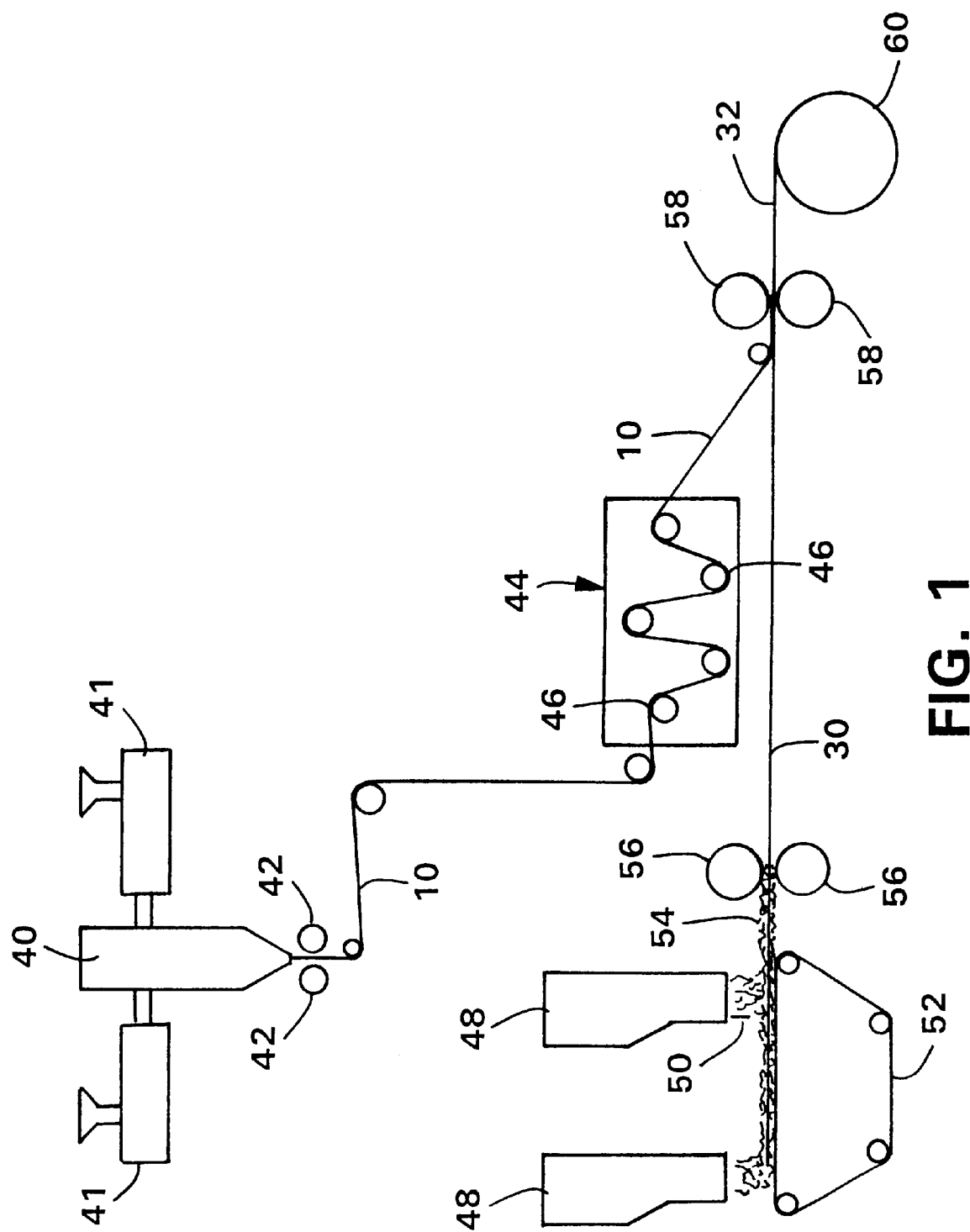
FIG. 1 is a schematic illustration of a process for making the composite material of the present invention.

Referring to FIG. 1, the illustrated process begins with extruders 41 supplying film die 40 forming a filled coextruded film 10 directed through guide rolls 42, rotating over support rolls to machine direction orientation section 44. During the orientation process, the temperature of the film 10 will depend on the composition of the film as well as the breathability and other desired end properties of the composite material. For example, as a loop fastener, the amount of retraction will affect the size of pillowed nonwoven. In most cases the film will be maintained at a temperature no higher than 10° C. below its melting point. The purpose for heating the film is to allow it to be stretched quickly without causing film defects. The heated film is stretched in the machine direction in a machine direction orientor section 44 comprising rotating rolls 46. Rolls 46 may be driven at increasing speeds with the result that the film is stretched in the direction of travel ("machine direction" or"MD"). The amount of stretching will depend on the desired end properties of the loop fastener, but, in general, the film will be stretched to at least about 300% of its original length but less than the amount that tends to result in film defects. For most applications with films based on polyolefins, for example, the stretch will be to at least 200% of the original film length and, frequently, in the range of about 250% to 500%. A nonwoven forming section, for example including spunbond formers 48 extrude filaments 50 onto support 52 forming web 54 directed to a bonding nip formed by rolls 56. Prebonded spunbond web 30 is laminated to film 10 using a second pattern at the nip between rolls 58. After niplaminating, with or without heat, the two layers are allowed to relax, and the laminate is wound at a reduced speed, for example, 80% to 90% of the nip speed that permits film 10 to retract to cause puckering of facing layer 30. After retraction, the combined layers may be annealed by contact with a heated roll or the like which is driven at about line speed to avoid significant additional stretching. The annealing temperature will vary according to the desired end properties of the loop fastener material and the composition of the layers, but may be, for example, within 15° C. of the temperature used in stretching. After annealing, the combined layers may be cooled, for example, by contact with air from air knife or chill rolls, if desired, or collected directly as roll 60 or directed to a converting line for incorporation into a personal care product.

As will be apparent to those skilled in the art, the above process is adaptable to many films and facing layers to produce breathable or nonbreathable barrier loop fastener material having widely varying properties. To work effectively as a loop fastener material in accordance with the invention, however, selection of these components desirably takes into consideration a number of factors. The film at the low weights, for example, must be robust enough to withstand the process steps necessary to provide desired flexibility and softness as well as to maintain low cost. In addition, the film must be capable of bonding effectively to the facing layer and maintaining barrier properties and moisture vapor transmission rates. For many applications it will be desired that the stretched film provide opacity to the composite as well.

Films meeting these requirements include polymers, such as polyethylene, polypropylene, blends including polyolefins and copolymers such as ethylene and propylene copolymers, for example generally having a basis weight in the range of from about 10 gsm to about 50 gsm, advantageously for loop component applications, in the range of from about 15 gsm to about 30 gsm. Specific examples include linear low density polyethylenes such as Dowlex® 2535, 3347 and 3310, Affinity® 5200 available from Dow Chemical Company of Midland, Mich. The film compositions desirably contain at least about 40% by weight of a filler such as calcium carbonate and especially about 45% to about 65% by weight of such filler. Examples include Supercoat® calcium carbonate from English China Clay of Sylacauga, Ala. which contains a coating of about 1.5% by weight of either stearic acid or behenic acid to enhance dispersion of the filler. Particularly advantageous film examples include coextruded films having on one or both sides a thin, external layer of an amorphous polymer such as a propene-rich polyalphaolefin terpolymer or copolymer which allows bonding to the facing layer without requiring a separately applied bonding layer. An example is Catalloy polymer from Montell USA, Inc. of Wilmington, Del. which is an olefinic multistep reactor product wherein an amorphous ethylene propylene random copolymer is molecularly dispersed in a predominantly semicrystalline high propylene monomer/low ethylene monomer continuous matrix, an example of which is described in U.S. Pat. No. 5,300,365 to Ogale. In addition, the amorphous polymer layer may also include hot melt adhesives or other amorphous polyalphaolefin resins, which desirably have a melt viscosity of 100,000 mPa sec or greater, in an amount of, for example, up to about 100% by weight of the layer. Commercially available amorphous polyalphaolefins, such as those used in hot melt adhesives, are suitable for use with the present invention and include, but are not limited to, REXTAC® ethylene-propylene APAO E-4 and E-5 and butylene-propylene BM-4 and BH-5, and REXTAC® 2301 from Huntsman Corporation of Salt Lake City, Utah, and VESTO-PLAST® 792 from Huls AG of Marl, Germany. These amorphous polyolefins are commonly synthesized on a Ziegler-Natta supported catalyst and an alkyl aluminum co-catalyst and the olefin, such as propylene, is polymerized in combination with varied amounts of ethylene, 1-butene, 1-hexane or other materials to produce a predominantly atactic hydrocarbon chain. Also useful are certain elastomeric polypropylenes such as are described, for example, in U.S. Pat. No. 5,539,096 to Yang et al. and U.S. Pat. No. 5,596,092 to Resconi et al., incorporated herein by reference in their entireties, and polyethylenes such as AFFINITY®, EG 8200, from Dow Chemical of Midland, Mich. as well as EXACT® 4049, 4011 and 4041 from Exxon of Houston, Tex., as well as blends including one or more tackifiers and KRATON® from Shell Chemical Company of Houston, Tex. A composite with the bonding layer on one side only may have the advantage of a higher moisture vapor transmission rate if desired. Such films are described in greater detail in coassigned U.S. patent application Ser. No. 08/929, 562 now U.S. Pat. No. 6,045,900 filed on even date herewith in the names of McCormack and Haffner and entitled "Breathable Filled Film Laminate"the contents of which are incorporated herein in their entirety by reference. Other film layers will be apparent to those skilled in the art in light of the examples provided herein.

The prebonded facing layer will be selected so as to be compatible with the film or bonding layer and will have properties such as basis weight, bulk, and strength adequate for the intended use. Primarily for economic reasons, nonwoven webs are preferred, especially spunbonded nonwovens having a basis weight generally in the range of from about 10 gsm to about 50 gsm, for example, frequently within the range of from about 15 gsm to about 25 gsm. The composition of the facing layer will be selected to be compatible with the film layer while providing the desired properties in the loop fastener component. Generally useful are synthetic polymers such as polyolefins, for example, polypropylene, polyethylene, blends and copolymers including propylene and ethylene. Such nonwovens are described above and in the references provided herein, and their manufacture is known to those skilled in this art. Specific examples include ACCORD® spunbond nonwovens available from Kimberly-Clark Corporation, Dallas, Tex. The bond pattern, for the facing layer, as mentioned above, will provide for looping between bonds to provide attachment areas for complementary hooks. Useful examples include an expanded RHT pattern as illustrated in U.S. Design Pat. No. 239,566 to Vogt, an EHP pattern, a Delta Dot pattern which comprises rows of offset circular bonds having about 102 pins/in.$^2$ for a bond area of 9% to 20%, and a Ramish pattern as above described. One advantageous bond pattern for a spunbond facing web is a "S" weave pattern as described in coassigned, contemporaneously filed U.S. patent application Ser. No. 08/929,808 now U.S. Pat. No. 5,964,742 in the names of McCormack, Fuqua, and Smith and entitled "Nonwoven Bonding Patterns Producing Fabrics with Improved Strength and Abrasion Resistance" which is incorporated herein by reference in its entirety. In all cases the % bond area will be less than about 30% for example, about 5% to about 30% and desirably from about 10% to about 25%, and desirably in the range of from about 75 to about 125/in.$^2$. The bond density will be from about 50 to about 200/in.$^2$. In addition, for the application for the loop fastener component, the facing will desirably have a tensile strength, measured as described above, of at least about 3000 g taken in the machine direction, and at least about 1500 g taken in the cross-machine direction, and advantageously a Martindale abrasion, measured as described above, of at least about 3.

When used, the separately applied amorphous polymer bonding layer will be compatible with both facing and film layers and provide bonding between them without preventing moisture vapor transmission. Advantageously the bonding layer is applied by meltblowing, for example, an amorphous polyolefin such as REXTAC® 2730 or 2330 available from Huntsman Corporation, Salt Lake City, Utah. The meltblown layer when applied at low weights, for example, less than 10 gsm, advantageously less than 5 gsm, is breathable and cost effective. Other examples include Vestoplast® 703, 704 and 508 from Huls AG of Marl, Germany and National Starch NS 5610 from National Starch Chemical Company of Bridgewater, N.J., and the elastomeric compositions described above.

Whether bonded with or without the separately applied bonding layer, the bond strength between the facing and the film as measured by the above described laminate peel test will desirably exceed the peel strength between the hook facing and the complementary hook as measured by the above described hook peel test, so as to prevent undesired delamination. Advantageously, the difference is at least about 100 g. In addition, for many applications and particularly as a backing for a personal care article such as a diaper, for example, the composite will have a hydrohead, as measured by the hydrohead test described in the test method section, of at least about 50 mbar at first drop and advantageously at least about 90 mbar. Especially when used as a backing for disposable personal care products, the composite will have a moisture vapor transmission rate of at least about 100 g/m$^2$/24 hours and advantageously at least about 800 g/m$^2$/24 hours. For these applications, a hook peel strength as measured by Federal Test Standard 191A, Method 5514 will desirably exceed 100 g and a hook shear strength, as measured by the procedure described in the test method section, will desirably exceed 1500 g.

Figure 2:
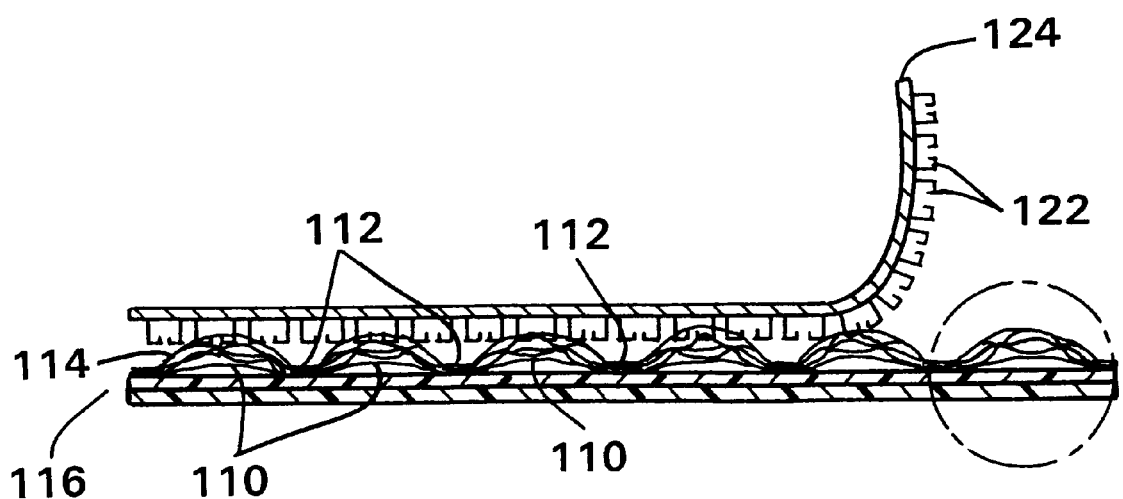
FIG. 2 is a cross-section of one embodiment of a loop fastener using the composite material of the present invention.
Figure 2A:
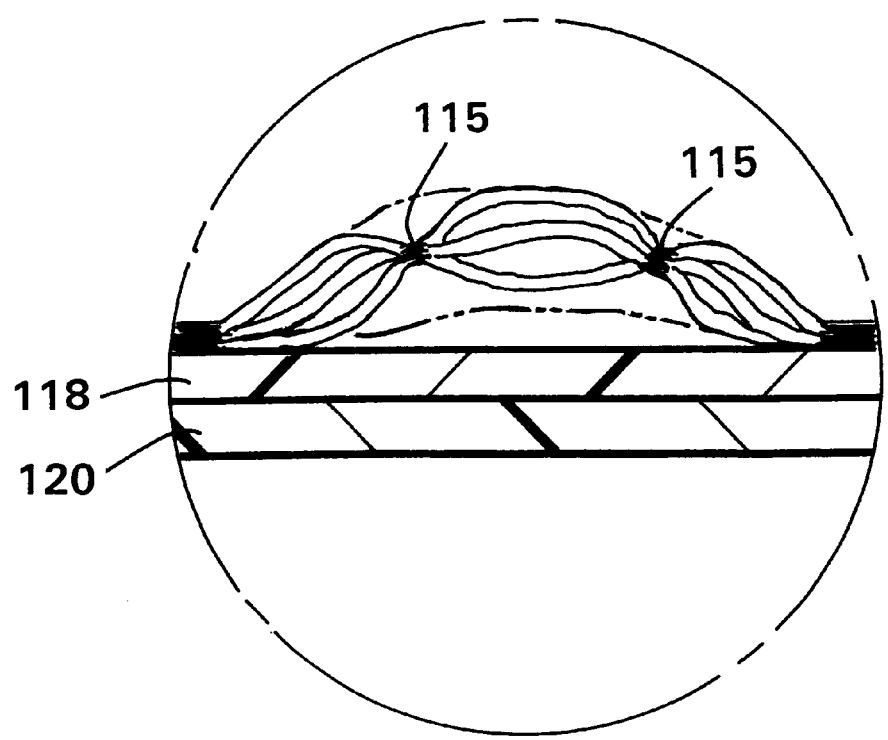
FIG. 2A is an enlargement representative of the area in the circle of FIG. 2.

Referring to FIG. 2, there is shown in cross-section an embodiment of a loop fastener component of the present invention. Facing layer 114 of, for example, spunbond, contains a pattern of prebond areas 115 (FIG. 2A) that is different from the pattern of laminate bonds 112. Loops 110 between laminate bond areas 112 are formed in spunbonded facing layer 114 which is bonded to a coextruded film 116 containing a bonding side or layer 118 and base layer 120 at each of the laminate bonds 112. As shown, loop areas 110 are comprised of filaments or fibers unbonded to the coextruded film 116 and available to entangle hook members 122 of complementary hook member 124. As shown, the hook and loop layers are partially separated for clarity. FIG. 2A is a representation of an enlargement of the area shown in the circle of FIG. 2 and shows the separate patterns of prebonded nonwoven bonds 115 and laminate bonds 112.

Figure 3:
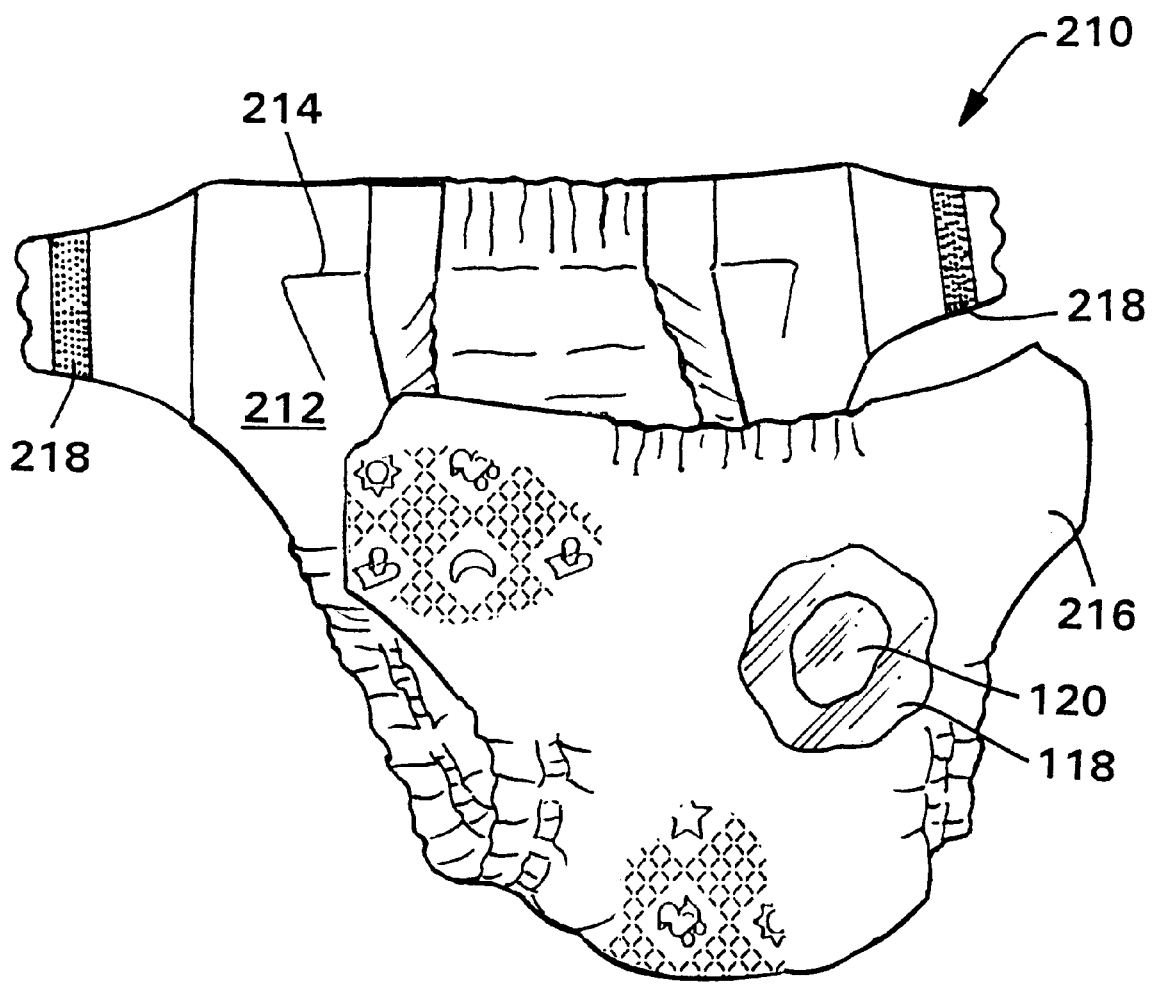
FIG. 3 is an illustration of a loop fastener material of the present invention in use as a backing component of a personal care product.

Referring to FIG. 3, an example of the loop fastener component of the present invention in the form of a backing material for a disposable personal care diaper product is shown. Diaper 210 comprises liner 212, absorbent 214 and backing 216. As is generally known, the liner 212 permits urine to pass through and be absorbed by absorbent 214 while the backing 216 (shown partially broken away showing layers 118 and 120 (FIG. 2A) for clarity) is impervious to urine to help avoid leakage. In this case the entire backing is formed from a loop fastener material of the present invention, and as described in connection with FIG. 2, with the nonwoven loops on the outside. This provides an essentially infinite degree of adjustment when combined with hook fastener elements 218. In use, the hook elements 218 can be pulled to a snug fit and fastened anywhere on the backing 216. Furthermore, if adjustment in the fit is desired, the hook elements 218 may be simply peeled away and repositioned anywhere on the backing 216. In advantageous embodiments, the backing is pervious to moisture vapor for increased comfort and dryness.

Figure 4:
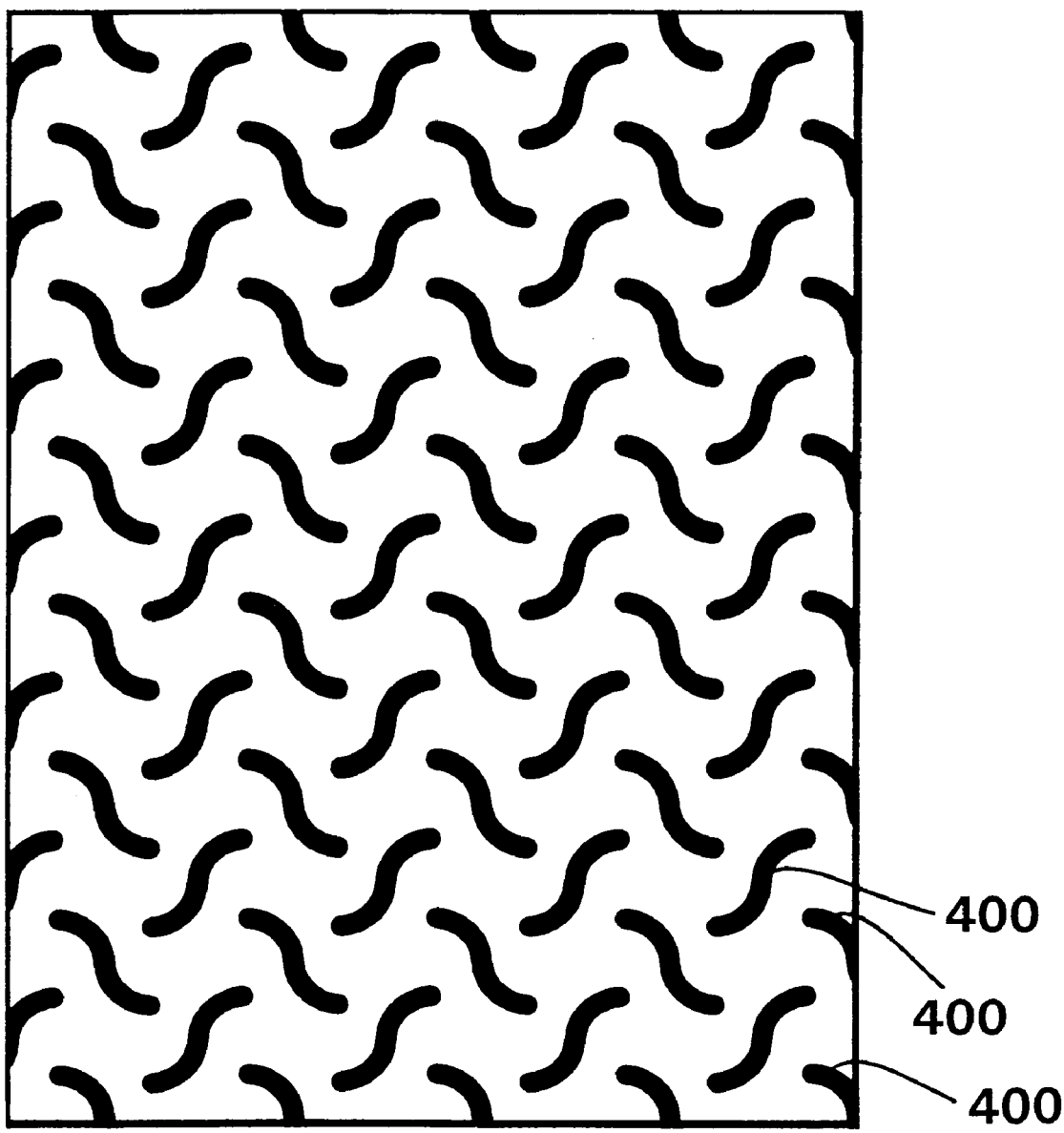
FIG. 4 is an illustration of one nonwoven bond pattern useful in accordance with the present invention.
Figure 5:
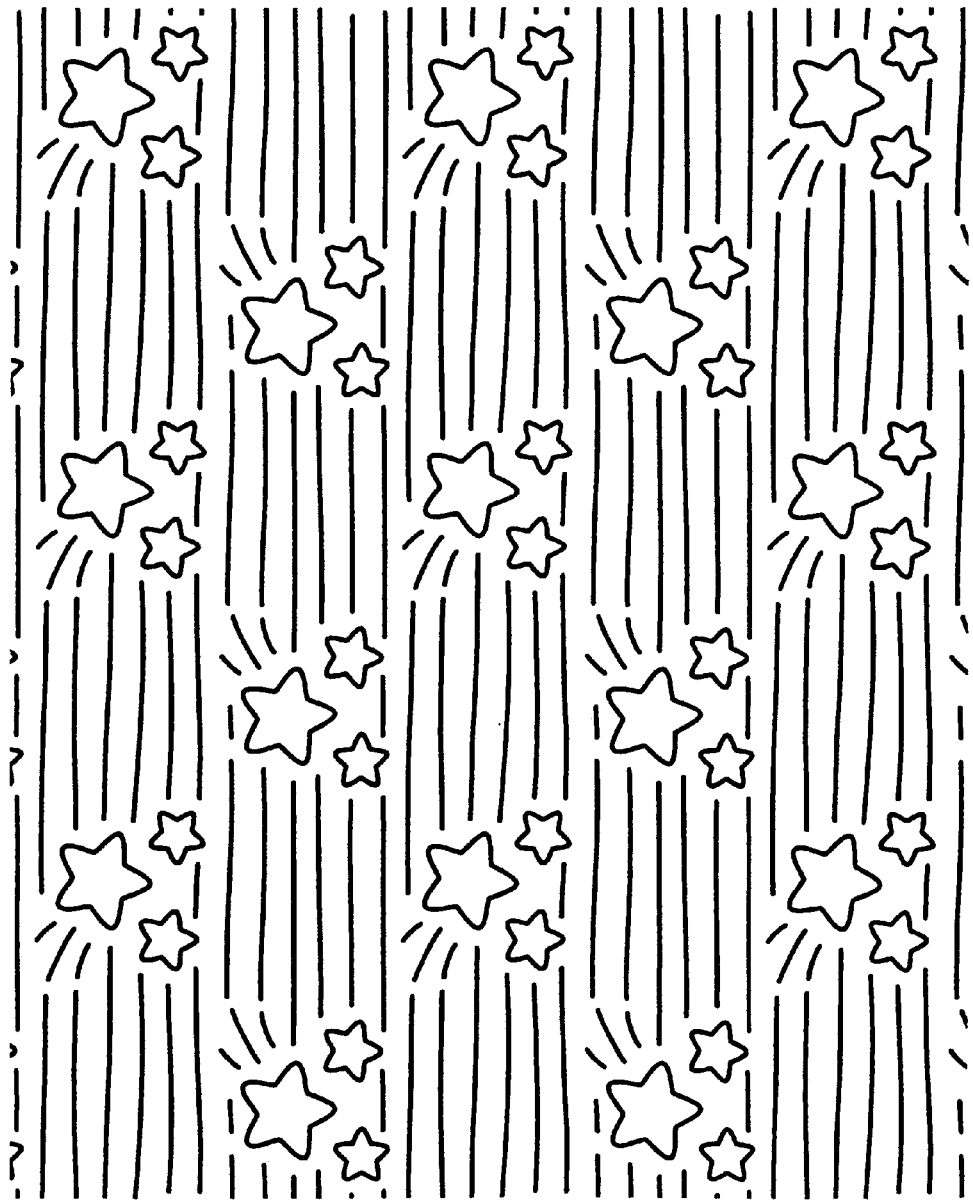
FIG. 5 is an illustration of a lamination bond pattern useful in accordance with the present invention.
Figure 6:
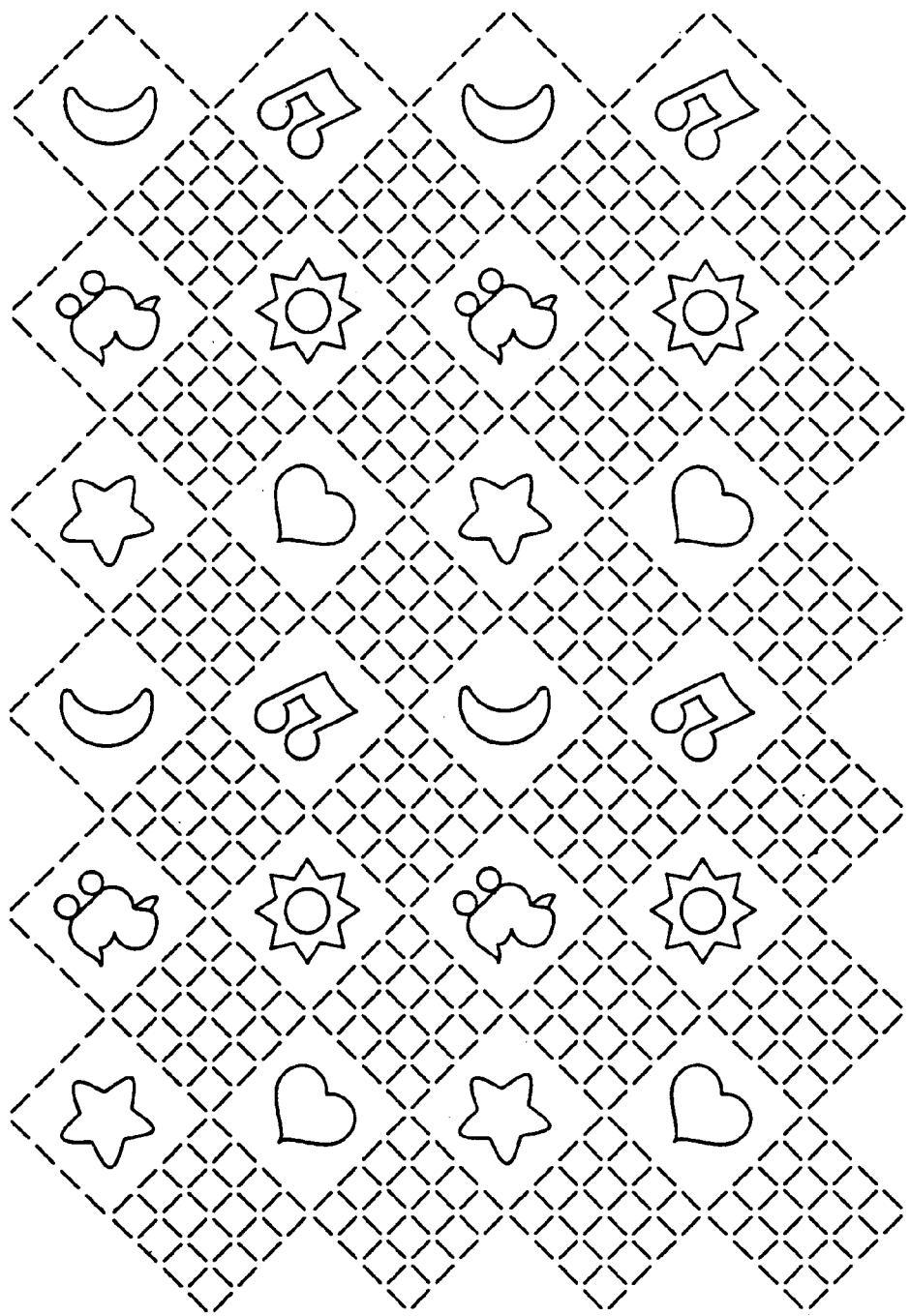
FIG. 6 is an illustration of a second lamination bond pattern useful in accordance with the present invention.

FIGS. 5 and 6 illustrate representative laminate patterns useful in accordance with the prebonded nonwoven component of the composite of the present invention. FIG. 4 shows "Baby Objects" as described above with prebond areas 400, and FIG. 5 shows "C-Star" as described above with bond areas 500.

EXAMPLES

For the following examples, a procedure as shown in FIG. 1 was used to form a loop fastener component, except as otherwise indicated.

Example 1

For this example the facing was a spunbond fabric of 2.0 denier filaments made from a copolymer of propylene with 3.5% ethylene (Union Carbide 6D43 available from Union Carbide Corporation of Danbury, Conn.) and having the basis weight of about 0.7 osy (about 24 gsm) having been bonded with a "S-weave" pattern with a bond density of 111 pins/in2 (17.2 pins/cc) and 17.7 actual measured bond area as described in copending and coassigned U.S. patent application Ser. No. 08/929,808, filed Sep. 15, 1997 in the names of McCormack et al and entitled "Nonwoven Bonding Patterns Producing Fabrics with Improved Strength and Abrasion Resistance" now U.S. Pat. No. 5,964,742, the entire contents of which is incorporated herein by reference. The film was a cast "AB" film having a base layer of 45% LLDPE (Dowlex®NG3310, 0.918 g/cc density, melt index at 190° of 3.5 g/10 min. Available from Dow Chemical Co. of Midland, Mich.), 50% Supercoat™, a ground, stearic acid coated CaCO3(avaialble from English China Clay Co. of Sylacauga, Ala. and 5% LDPE(Dow 4012, 0.916 g/cc density, melt index at 190° C. of 12.0 g/10 min. available from Dow Chemical Co. of Midland, Mich.) and a bonding layer on one side containing 60% Supercoat™ $CaCO_3$, 20% amorphous propene-rich polyalphaolefin ("APAO"), (Huls Vestoplast®, 0.865 g/cc density, melt viscosity at 190° C. of 125,000 mPa according to DIN 53 019, available form Huls America, Inc of Somerset, N.J.) and 20% elastomeric polyethylene (Dow Affinity® EG8200 constrained geometry catalyzed, density 0.87 g/cc, melt index at 190° C. of 5.0 g/10 min, available from Dow Chemical Co. of Midland, Mich.). The base layer constituted 90% by weight, and the bonding layer 10% by weight. The total basis weight of the coextruded film was 58 gsm (about 1.5 mil). The stretching of the film included a preheating step of 50° C., stretching in a single zone 3.8× in the machine direction at 66° C. at 211 ft/min(64 m/min) the film was annealed at 82° C. This stretched film was successfully bonded at 191 ft/min(58 m/min) at 175PLI with the "Baby Objects" bond pattern (U.S. Design Pat. No. 356,688 to Uitenbroek et al. dated Mar. 28, 1995) at 92° C. pattern temperature and 66° C. smooth steel anvil temperature. The laminate was allowed to relax 2.5% (bonder speed: 191 ft/min(53 m/min) winder speed 186 ft/min(57 m/min)) then later the laminate was reheated to 92° C. and relaxed an additional 4%. The resulting laminate had a basis weight of 43 gsm, hydrohead of 101 mbar of water, a laminate peel strength of 490 g and WVTR of 127 g/m2/24 hr. When tested with a complementary hook Velcro 51,1003, from Velcro International of Manchester, N.H., a hook peel of 167 g and hook shear of 3239 g was obtained based on an average of ten tests.

Example 2

For this example the facing was a spunbond fabric of 2.0 denier filaments made from a copolymer of propylene with 3.5% ethylene (Union Carbide 6D43 available from Union Carbide Corporation of Danbury, Conn.) and having the basis weight of about 0.7 osy (about 24 gsm) having been bonded with a "S-weave" pattern with a bond density of 111 pins/in2 (17.2 pins/cm$^2$) and 17.7 actual measured bond area as described in copending and coassigned U.S. patent application Ser. No. 08/929,808, filed Sep. 15, 1997, in the names of McCormack et al and entitled "Nonwoven Bonding Patterns Producing Fabrics with Improved Strength and Abrasion Resistance", now U.S. Pat. No. 5,964,742 the entire contents of which is incorporated herein by reference. The film was a cast "AB" film having a base layer of 45% LLDPE (Dowlex® NG3310, 0.918 g/cc density, melt index at 190° of 3.5 g/10 min. Available from Dow Chemical Co. of Midland, Mich.), 50% Supercoat™, a ground, stearic acid coated CaCO3(avaialble from English China Clay Co. of Sylacauga, Ala. and 5% LDPE(Dow 4012, 0.916 g/cc density, melt index at 190° C of 12.0 g/10 min. available from Dow Chemical Co. of Midland, Mich.) and a bonding layer on one side containing 60% Supercoat™ $CaCO_3$, NJ) and 40% elastomeric polyethylene (Dow Affinity® EG8200 constrained geometry catalyzed, density, (0.87 g/cc, melt index at 190° C. of 5.0 g/10 min, available from Dow Chemical Co. of Midland, Mich.). The base layer constituted 85% by weight, and the bonding layer 15% by weight. The total basis weight of the coextruded film was 58 gsm (about 1.5 mil). The stretching of the film included a preheating step of 50° C., stretching in a single zone 3.8× in the machine direction at 66° C. at 400 ft/min(61 m/min) the film was annealed at 82° C. This stretched film was successfully bonded at 370 ft/min(113 m/min) at 175 PLI with the "Baby Objects" bond pattern (U.S. Design Pat. No. 356,688 to Uitenbroek et al. dated Mar. 28, 1995) at 110° C. pattern temperature and 82° C. smooth steel anvil temperature. The laminate was allowed to relax about 6.7% (bonder speed: 370 ft/min(113 m/min) winder speed 345 ft/min(105 m/min)). The resulting laminate had a basis weight of 43 gsm, hydrohead of 59 mbar of water, a laminate peel strength of 172 g and WVTR of 449 g/m2/24hr. When tested with a complementary hook Velcro 51,1004, a hook peel of 177 g and hook shear of 1822 g; and with Velcro 51,1003 a hook peel of 114 and a hook shear of 3236 g was obtained based on an average of ten tests.

For comparison, samples of conventional nonwoven/film laminate diaper backings were tested with the same hook components used in the preceding examples. The following results were obtained: Kimberly-Clark Corporation's Huggies® Ultratrim™1996 commercial product nonwoven-film laminate outercover (polypropylene 2.5 denier spunbond bonded with wireweave pattern: 302 pins/in.$^2$, 18% bond area) when tested with Velcro hook 858, a hook peel of 29 g and a hook shear of 171 g were obtained on an average of 10 tests. With the Velcro 51-1003 hook, a hook peel of 71 g and a hook shear of 589 g were obtained on an average of 10 tests. It has been determined with consumer use tests that a hook peel of at least about 100 g and hook shear of at least about 1500 g are desired for primary fastening of the product for active toddlers.

Those of skill in this art will recognize that the invention is subject to many variations, modifications and equivalents within the scope of the foregoing description. It is intended that all such modifications, variations and equivalents be included as are embraced by the appended claims. For these purposes equivalents include functional as well as structural and compositional equivalents. For example, a nail and a screw are functional fastener equivalents even though they may be of different structures.

We claim:

1. A laminate composite comprising:
    a prebonded nonwoven having a surface area containing a pattern of spaced apart bonds with a frequency in the range of from about 50 to about 200 per square inch and comprising about 10% to about 30% of said surface area with unbonded fibers or filaments forming loops between said bonds, and
    a retracted microporous film comprising an amorphous polymer and bonded to said nonwoven at laminate bond locations comprising a pattern on the laminate surface area having spaced apart laminate bonds formed by said amorphous polymer, said laminate bonds forming a pattern that is different from said nonwoven pattern of spaced apart bonds, said film being otherwise substantially unbonded to said nonwoven, and wherein said nonwoven contains a plurality of prebond bonds in each area where it is substantially unbonded to said film.

2. The composite of claim 1 wherein said composite has a moisture vapor transmission rate of at least about 100 g/m$^2$/24 hr. and a hydrohead value of at least about 50 mbar of water.

3. The composite of claim 1 wherein said spaced apart bonds comprise a bond frequency in the range of from about 75 to about 125 per square inch.

4. The composite of claim 2 wherein said spaced apart bonds comprise a bond frequency in the range of from about 75 to about 125 per square inch.

5. The composite of claim 3 wherein said laminate bonds cover less than 30% of the laminate surface area.

6. The composite of claim 4 wherein said laminate bonds cover less than 30% of said laminate surface area.

7. The composite of claim 1 wherein said film comprises a plurality of layers and said amorphous polymer comprises one of said layers that is in contact with said nonwoven.

8. The composite of claim 1 wherein said amorphous polymer comprises a layer separately applied to said film prior to contact with said nonwoven.

9. The composite of claim 2 wherein said fibers or filaments between said spaced apart bonds are looped forming engagement areas for attachment to a complementary hook fastener component providing hook peel strength and hook shear strength.

10. The composite of claim 9 as a loop component of a hook and loop fastening system wherein the hook peel strength is in the range of from about 100 g to about 800 g.

11. The composite of claim 10 wherein the hook shear strength is in the range of from about 1000 g to about 6000 g.

12. A personal care article comprising one or more components selected from the group consisting of a liner, absorbent layer, and a backing and having hook and loop fastening means wherein said loop means comprises the composite of claim 1.

13. A personal care article comprising the composite of claim 5.

14. The personal care article of claim 13 wherein said composite comprises a backing material providing fastenability substantially anywhere on said backing.

15. The personal care article of claim 14 selected from the group consisting of diapers, training pants, incontinent wear and feminine care products.

16. A mechanical fastener comprising hook and loop components wherein the loop component comprises the composite of claim 4.

17. A mechanical fastener comprising hook and loop components wherein the loop component comprises the composite of claim 5.

18. The composite of claim 5 wherein the spaced apart laminate bonds comprise about 10% to about 25% of said prebonded nonwoven surface area.

19. The composite of claim 18 having a Martindale abrasion of at least about 3.

20. The composite of claim 19 having a moisture vapor transmission rate of at least about 800 g/m$^2$/24 hours and a hydrohead of at least 50 mbar.

21. A process for making a composite comprising the steps of:
    a) providing a prebonded nonwoven having a surface area containing a pattern of spaced apart bonds with a bond frequency in the range of from about 50 to about 200 per square inch and comprising about 10% to about 30% of said surface area with unbonded fibers or filaments forming loops between said bonds,
    b) providing a breathable, microporous film,
    c) providing a layer of an amorphous polymer between said nonwoven and said film, and
    d) combining said nonwoven, amorphous polymer layer and microporous film under stretching and retracting conditions such that said nonwoven becomes bonded to said film in a pattern of spaced apart bonds different from said prebonded nonwoven pattern and covering less than 30% of the surface area.

22. The process of claim 21 wherein said film is stretched and retracted after bonding to said nonwoven causing fibers or filaments to loop between said spaced apart bond area providing areas of attachment for a complementary hook component.

* * * * *

UNITED STATES PATENT AND TRADEMARK OFFICE
CERTIFICATE OF CORRECTION

PATENT NO. : 6,589,638 B1
DATED : July 8, 2003
INVENTOR(S) : McCormack et al.

It is certified that error appears in the above-identified patent and that said Letters Patent is hereby corrected as shown below:

Column 11,
Lines 28 and 29, "above with prebond areas 400, and" should read -- above, and --
Lines 29 and 30, "described above with bond areas 500" should read -- described above. --
Line 27, "FIG. 4 shows" should read -- FIG. 6 shows --

Signed and Sealed this

Seventh Day of September, 2004

JON W. DUDAS
*Director of the United States Patent and Trademark Office*